(12) United States Patent
Pani (10) Patent No.: US 9,362,013 B2
(45) Date of Patent: Jun. 7, 2016

(54) TILTING COLLIMATOR, IN PARTICULAR FOR SINGLE-PHOTON EMISSION COMPUTED TOMOGRAPHY

(71) Applicants: KAY SYSTEMS ITALIA S.r.l., Rome (IT); UNIVERSITA' DEGLI STUDI DI ROMA LA SAPIENZA, Rome (IT)

(72) Inventor: Roberto Pani, Rome (IT)

(73) Assignees: KAY SYSTEMS ITALIA S.R.L., Rome (IT); UNIVERSITA' DEGLI STUDI DI ROMA LA SAPIENZA, Rome (IT)

( * ) Notice: Subject to any disclaimer, the term of this patent is extended or adjusted under 35 U.S.C. 154(b) by 0 days.

(21) Appl. No.: 14/434,819

(22) PCT Filed: Oct. 11, 2013

(86) PCT No.: PCT/IB2013/059313
§ 371 (c)(1),
(2) Date: Apr. 10, 2015

(87) PCT Pub. No.: WO2014/057472
PCT Pub. Date: Apr. 17, 2014

(65) Prior Publication Data
US 2015/0279493 A1 Oct. 1, 2015

(30) Foreign Application Priority Data
Oct. 11, 2012 (IT) .............................. RM2012A0485

(51) Int. Cl.
*G21K 1/02* (2006.01)
*A61B 6/03* (2006.01)

(52) U.S. Cl.
CPC ................ *G21K 1/025* (2013.01); *A61B 6/037* (2013.01)

(58) Field of Classification Search
CPC ......... G21K 1/025; G21K 1/06; G21K 1/062; A61B 6/037; A61B 6/4258; A61B 6/4233; A61B 5/06; G01T 1/1644; G01T 1/243; G01T 1/244; G01T 1/2985; G21F 5/04
USPC ................ 250/363.1, 363.02, 361 R, 363.04, 250/363.05, 366, 367, 393, 394, 397; 378/149, 150, 153
See application file for complete search history.

(56) References Cited

U.S. PATENT DOCUMENTS 3,790,782 A * 2/1974 Inoue ....................... A61B 6/06
250/361 R
3,937,969 A * 2/1976 Muehllehner .......... G21K 1/025
250/363.02

(Continued)

FOREIGN PATENT DOCUMENTS

WO 2004042546 A1 5/2004
WO 2010008539 A1 1/2010

*Primary Examiner* — David A Vanore
(74) *Attorney, Agent, or Firm* — Volpe and Koenig, P.C.

(57) ABSTRACT

A tilting collimator (4), in particular usable in the single photon emission computed tomography imaging technique, comprises: a plurality of side-by-side tubular structures (5), apt to form a matrix of tubular structures (5) on a two-dimensional space, each tubular structure (5) comprising at least a through hole; each tubular structure (5) being in contact with the tubular structures (5) adjacent thereto so as to be able to tilt only in presence of an equal tilting in the adjacent tubular structures (5); and retaining means, acting on the outer edges of said matrix, apt to move horizontally to determine the simultaneous tilting of all tubular structures (5) of the matrix, allowing a three-dimensional scanning of a gamma source by tilting progressively the single tubular structures (5) with great precision and in an extremely quick way.

15 Claims, 6 Drawing Sheets

(56) References Cited

U.S. PATENT DOCUMENTS

| | | | |
|---|---|---|---|
| 4,355,409 A | 10/1982 | Amplatz | |
| 4,419,585 A | 12/1983 | Strauss et al. | |
| 4,419,763 A * | 12/1983 | Hawman | A61B 6/483 250/363.1 |
| 4,597,096 A * | 6/1986 | Larsson | G01T 1/1642 250/363.1 |
| 4,672,648 A * | 6/1987 | Mattson | G21K 1/025 378/149 |
| 4,780,904 A * | 10/1988 | Winter | G21K 1/025 378/150 |
| 6,232,605 B1 * | 5/2001 | Soluri | G01T 1/1642 250/363.02 |
| 6,278,764 B1 * | 8/2001 | Barbee, Jr. | B82Y 10/00 378/84 |
| 6,583,420 B1 * | 6/2003 | Nelson | A61B 6/4233 250/363.05 |
| 6,603,123 B1 | 8/2003 | Zeng | |
| 6,806,474 B2 * | 10/2004 | McGregor | G01V 5/02 250/363.1 |
| 8,552,389 B2 * | 10/2013 | Jansen | A61B 6/037 250/363.1 |
| 2008/0042067 A1 | 2/2008 | Rousso et al. | |
| 2012/0108948 A1 | 5/2012 | Jansen et al. | |

* cited by examiner

TILTING COLLIMATOR, IN PARTICULAR FOR SINGLE-PHOTON EMISSION COMPUTED TOMOGRAPHY

The present invention relates to a tilting collimator, in particular usable in the imaging technique known as Single Photon Emission computed tomography (SPECT).

This technique of medical imaging of nuclear medicine uses gamma rays as ionizing radiation and it uses a so-called gamma camera to receive the image, but it allows processing a substantially three-dimensional image under the form of axial, sagittal or coronal sections.

The technique provides the ingestion, by the patient, of suitable radio drugs, for example $^{99m}$Tc-HMPAO (hexamethylpropylene amine oxime), to cause the localized emission of photons which have to be detected by the gamma camera.

The radio drug accumulates depending upon the specific metabolic functionality of the tissue or organ and with the same principle it can accumulate in the tumoral tissue. The detection of the radioactive isotope allows detecting the exact position of the tumour which could be then surgically removed or otherwise treated.

The operation of the gamma camera is based upon the capability of some crystals of generating photons of visible light when hit by the gamma radiation coming from the source. These photons are highlighted by using photomultipliers and transformed into electrical pulses.

The number of events detected in the time unit is proportional to the radioisotope concentration. Furthermore, the gamma radiation does not undergo alterations in its emission direction, thanks to the very high penetrating power thereof, and therefore such direction can be exploited to confer the requested three-dimensionality to the image which is processed.

Generally, in order to detect images, the gamma camera is rotated around the patient in order to obtain the scanning of planar images in the different projections obtained during the rotation.

The time necessary to obtain each protection is variable, but a duration of 15-20 seconds is typical. This involves a total scanning time of about 15-20 minutes, time range wherein the patient must remain immobile.

The range length also requests the ingestion of a strong dose of radio drug, which is potentially dangerous for the patient's health.

Therefore, one wishes to make the examination quicker and to decrease the ingested quantity of radio drug. Furthermore, the rotation of the gamma camera involves a removal of the same from the interesting site with the consequent deterioration of the spatial resolution and of the contrast, in particular for objects with small sizes.

The solution idea consists in providing a collimator allowing to receive photonic emission having a determined tilting, variable in time, without requesting the rotation of the gamma camera.

However, this collimator has to be able to implement a very precise collimation at predetermined angles, obtained by tilting members which, due to the shape thereof, can receive photons coming from one single direction.

The International patent application Nr. WO2010008538 describes an imaging technique of stereotactic type, wherein two sets of a plurality of metallic slats are tilted compared to a line perpendicular to the plane of the gamma camera. The tilting of the two groups of slats is specular, but this arrangement necessarily requires a very wide sensor and a precise alignment of the different slats during the tilting thereof and difficult to be obtained.

The U.S. Pat. No. 6,603,123 describes a collimator which, with respect to the previous one, comprises one single group of slats which is tilted. During this process, the slats can remain parallel therebetween or they can assume different angulations. However, in both cases, considering the requested precision, it is very difficult guaranteeing the exact positioning of each single slat, considering that the distance between the adjacent tilted slats varies upon varying the tilting itself.

At last, the U.S. Pat. No. 4,419,585 describes a tilting collimator too, obtained by overlapping a plurality of pierced plates, with the holes arranged coaxially one with respect to the other one.

By translating horizontally such plates by a different quantity from plate to plate: immobile the one nearest to the sensor and increasingly more and more moving away therefrom, a tilting of the holes resulting from said overlapping is obtained.

However, this arrangement too is very difficult to be controlled and, moreover, the resulting holes have step-like walls which decrease the resulting precision.

The technical problem underlying the present invention is to provide a collimator allowing to obviate the drawbacks mentioned with reference to the known art.

Such problem is thus solved by a collimator as specified above, characterizing in that it comprises:
  a plurality of side-by-side tubular structures, apt to form a matrix of tubular structures on a two-dimensional space; each tubular structure being in contact with the tubular structures adjacent thereto so as to be able to tilt only in presence of an equal tilting in the adjacent tubular structures, each tubular structure comprising at least a through hole; and
  retaining means, acting on the outer edges of said matrix, apt to move horizontally to determine the simultaneous tilting of all tubular structures of the matrix.

The main advantage of the tilting collimator according to the present invention lies in the fact of allowing a source scanning from different angles of the gamma source by tilting progressively the single tubular structures with great precision and in an extremely quick way.

The present invention will be described hereinafter according to a preferred embodiment thereof, provided by way of example and not with limitative purposes, with reference to the enclosed drawings wherein.

By referring to the FIGS. 1 to 4, a gamma camera is designated as a whole with 1. It comprises a not visible planar crystal towering above a photomultiplier 2 which, in turn, has a plurality of contacts 3.

Said crystal, constituting the upper face of the gamma camera, provides the resting base for a first collimator example, herein designated with 4, of tiltable type, apt to select the incidence angle of the gamma radiations coming from an organ which is subjected to single photon emission computed tomography (SPECT).

The collimator 4 comprises a plurality of side-by-side tubular structures 5 which, as a whole, are arranged side by side so as to form a matrix of tubular structures 7 on a plane two-dimensional space, that is substantially covering the whole surface of the crystal of the gamma camera 1.

The tubular structures 5 have to be meant stiff and they are made of a material impervious to the gamma radiation, in particular lead.

Each tubular structure 5 comprises at least a through hole 6 and it has a substantially parallelepiped-like shape, with outer plane and smooth walls.

Figure 1:
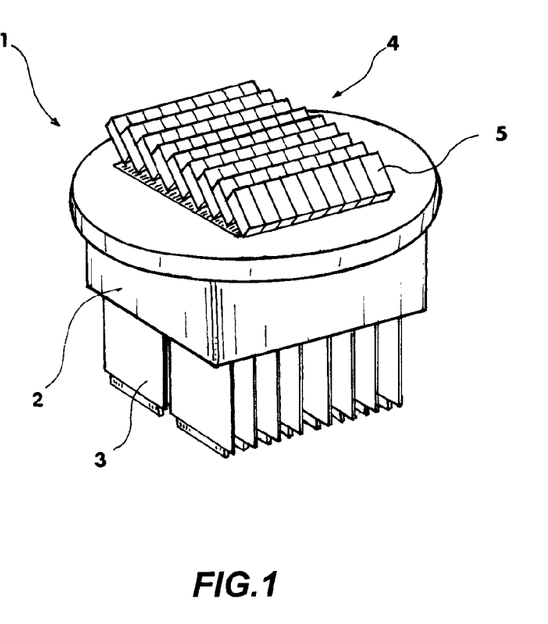
FIG. 1 shows a perspective view of a head of a gamma camera incorporating a first embodiment example of a tilting collimator according to the present invention.
Figure 2:
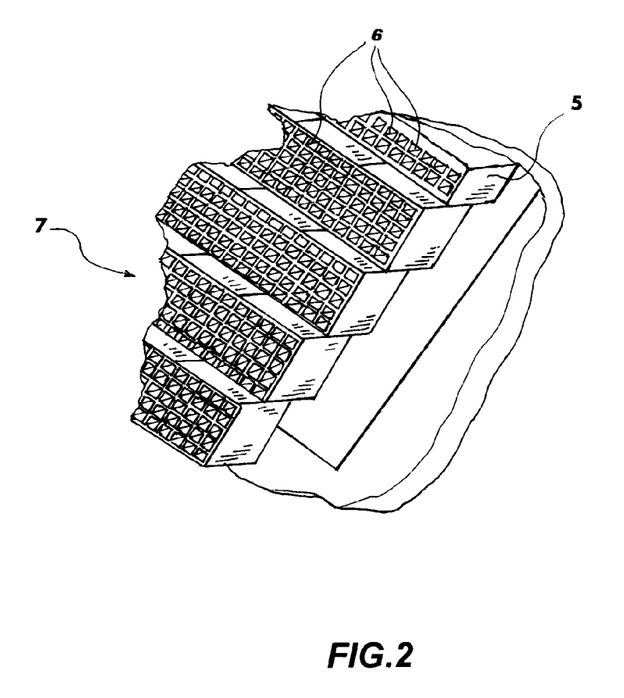
FIG. 2 shows an enlarged view of a detail of the collimator of FIG. 1.
Figure 3A:
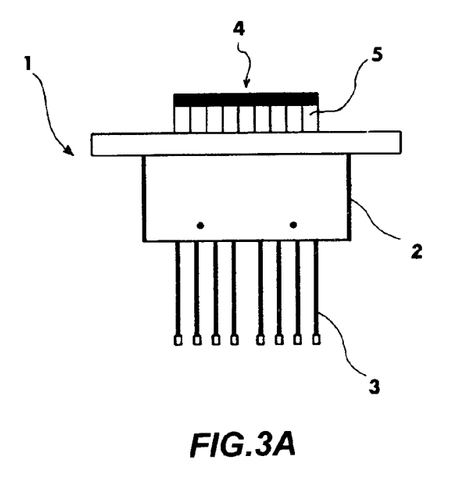
FIGS. 3A and 3B show a front view and a side view, respectively, of the gamma camera of FIG. 1.
Figure 3B:
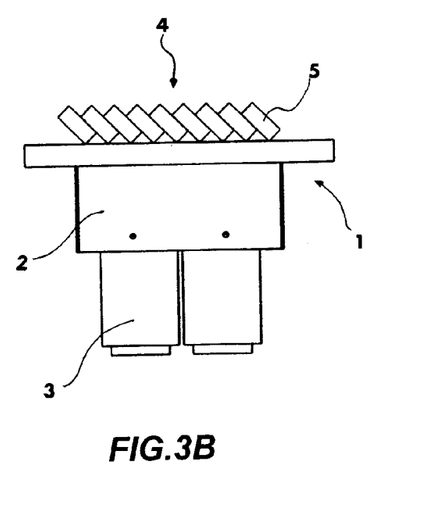
Figure 4:
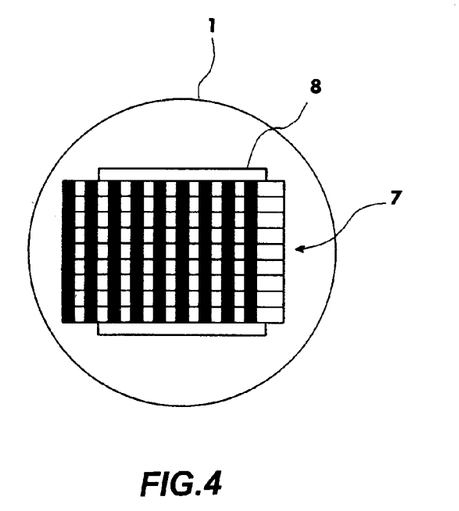
FIG. 4 shows a top plan view of the gamma camera of FIG. 1.

In the present embodiment example, each structure 5 is substantially grid-like shaped, comprising a squared basis and 25 holes: five lines each one with five holes.

By way of example, each hole has a squared section, with the purpose of minimizing the thickness of the lead walls separating them, with a cross size variable from 0.5 and 3.0 mm.

By considering the thickness of the walls, the whole cross sizes of each tubular structure vary from 5×5 mm to 20×20 mm.

The height of the tubular structure 5 could consequently vary between 10 mm and 50 mm, by guaranteeing that the height is always greater than the cross width of the structure 5.

The extension of the tubular structures 5 can cover even a surface of considerable entity, for example 800×400 mm.

It is meant however that the structure with 25 holes is only one of the possible ones, where it is possible using 16, 9, 4 or even one single hole per tubular structure, by obtaining the best compromise between mechanical stability and interaction between the side-by-side structures. Obviously, the squared section of the structure 5 is not an essential peculiarity, whereas the squared section of the single holes is preferred, even if it is possible using a hive-like structure with hexagonal holes or analogous configurations.

Each tubular structure 5 is in contact with the tubular structures adjacent thereto so as to be able to tilt only in presence of an equal tilting in the adjacent tubular structures 5.

Figure 7:
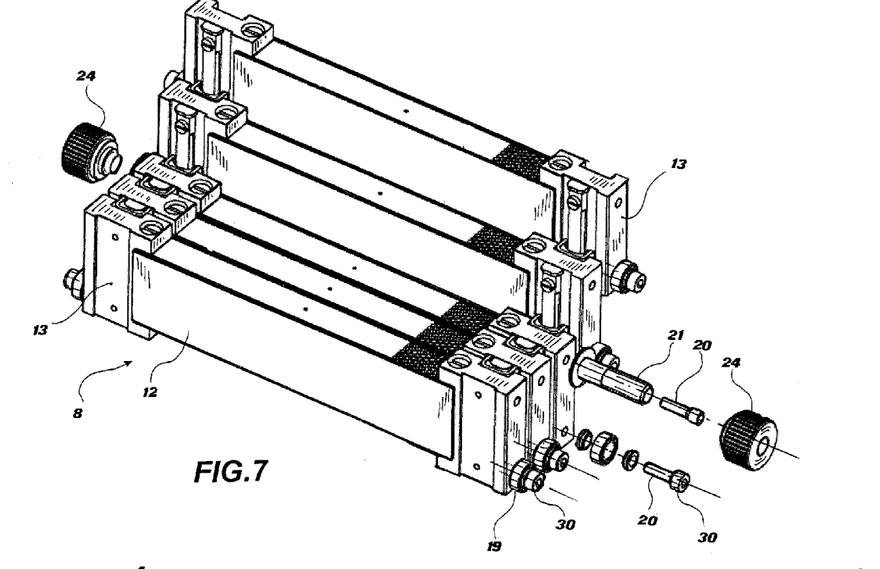
FIG. 7 shows a partially exploded axonometric view of a detail inside the collimator of FIG. 5.

In other words, it is possible tilting the structures 5 all together and by the same tilting, therefore the matrix 7 tilts in a single solution of prefixed angulation.

In order to obtain that, it is possible using retaining means 8 keeping all tubular structures 5 in a prefixed position one with respect the other one and to make the structures to translate at the respective distal end thereof, that is the one far from the crystal of gamma camera or in the immediate proximity.

To this regard, the collimator 4 comprises retaining means, acting on the outer edges of said matrix 7, apt to move horizontally to determine the simultaneous tilting of all tubular structures 5 of the matrix 8.

Preferably, the retaining means acts by contact at the distal end of the tubular structures 5 belonging to the edges of the matrix 7.

In particular, it is sufficient acting at said distal ends by pushing in horizontal direction on a matrix side and by accompanying the forward motion of the distal ends at the opposite side. On the other two sides, parallel to the pushing direction, it will be sufficient using a guide accompanying the tilting of the tubular structures 5.

In this way, a simple mechanical system can control with extreme precision the tilting of the tubular structures 5 of the whole matrix 7. A scanning could be then implemented in quick time, by tilting more and more the matrix by an angle with predetermined pitch.

By referring to figures from 5 to 12C, an additional embodiment example of the collimator according to the present invention is described; hereinafter the same numeral references will be used to designate analogous components.

Figure 5:
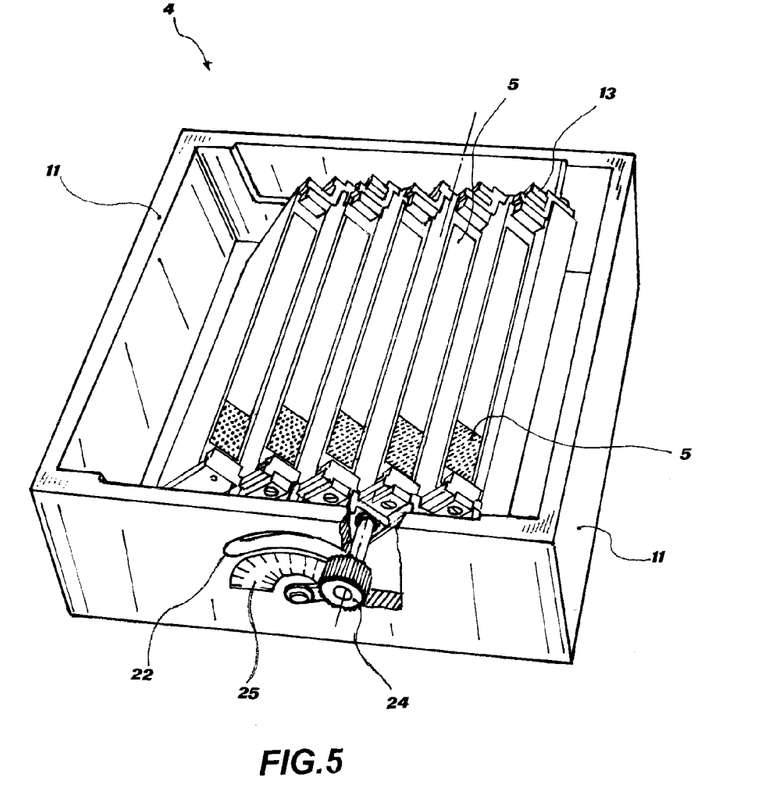
FIG. 5 shows a perspective view of a second embodiment example of a tilting collimator according to the present invention.
Figure 6:
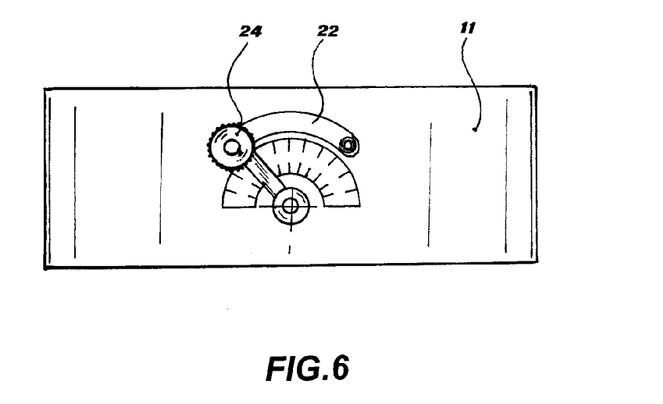
FIG. 6 shows a front view of the collimator of FIG. 5.

The second example of collimator 4 comprises a box-like structure 11 with substantially squared shape, having a periphery of fixed vertical walls.

Inside such structure, a plurality of tubular structures 5 is received which, in the present embodiment example, have the shape of a bar, that is an elongated parallelepiped extending from a wall of the box-like structure as far as the opposite wall.

The height of each tubular structure 5 is substantially analogous to that of the box-like structure 11 and the width is so as to allow the implementation of a certain number of through holes, which cross the structure in the height direction. The number of through holes is variable, for example they can be five or six, and they can be arranged by implementing a honeycomb scheme.

The bar, in turn, can be implemented by side-by-side tubular substructures.

The box-like structure 11 will contain then a plurality of side-by-side and parallel therebetween tubular structures 5, so as to cover the whole surface of the crystal of a gamma camera.

Analogously to the previous example, the tubular structures 5 have to be meant stiff and they are made of a material impervious to the gamma radiation, in particular lead.

Each tubular structure 5 is then in contact with the tubular structures adjacent thereto so as to be able to tilt only in presence of an equal tilting in the adjacent tubular structures 5.

In other words, it is possible tilting the structures 5 all together and by the same tilting, in a single solution of prefixed angulation.

In order to obtain that, it is possible using retaining means 8 keeping all tubular structures 5 in a prefixed position one with respect the other one and to make the structures to translate at the respective distal end thereof, that is the one far from the crystal of gamma camera or in the immediate proximity.

Figure 8:
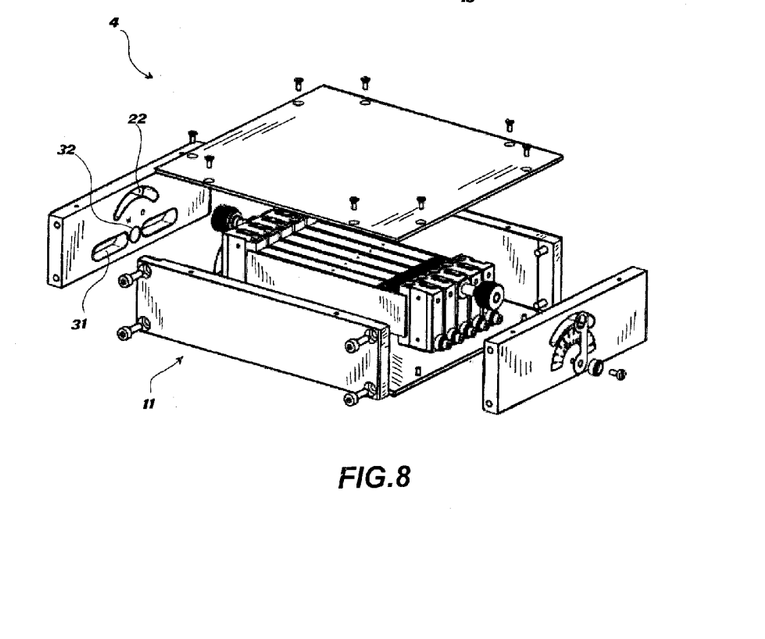
FIG. 8 shows a partially exploded axonometric view of the whole set of the collimator of FIG. 5.

In the present embodiment example, the retaining means, designated as a whole with 8, comprises a pair of slats 12 adhering laterally to the tubular structures 5, so as to contain them. At each end, each tubular structure 5 comprises respective fastening members 13 including a vice 14 which is able to be connected to the end of the tubular structure 5.

The fastening member 13 further comprises, on its own side surface, a system of mutual contact constituted on one side by a guide 15 obtained by fastening with suitable screws one slat having a U-shaped section with the concavity facing outwards. On the other side of the fastening member 13 the contact structure instead comprises a corresponding rib 16, obtained too by fastening with suitable screws a small bar 17 having, at its own lower and upper ends, a half-moon-like insert 18 the shape thereof is so as to be complementary to the the recess of the guide 15.

In this way each guide 15 can cooperate with the half-moon-like inserts 18 of the rib 16 of the adjacent tubular structure and viceversa.

Figure 10:
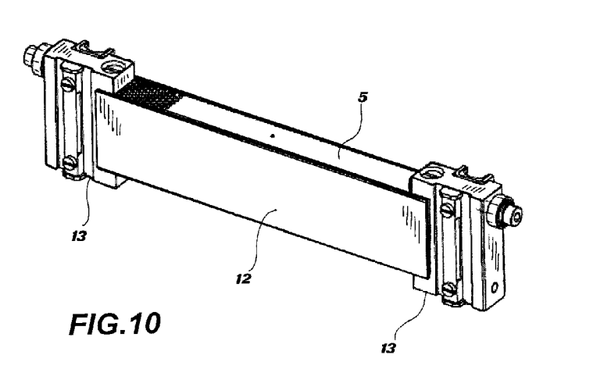
FIG. 10 shows a bottom and overturned axonometric view of the detail of FIG. 9.
Figure 11:
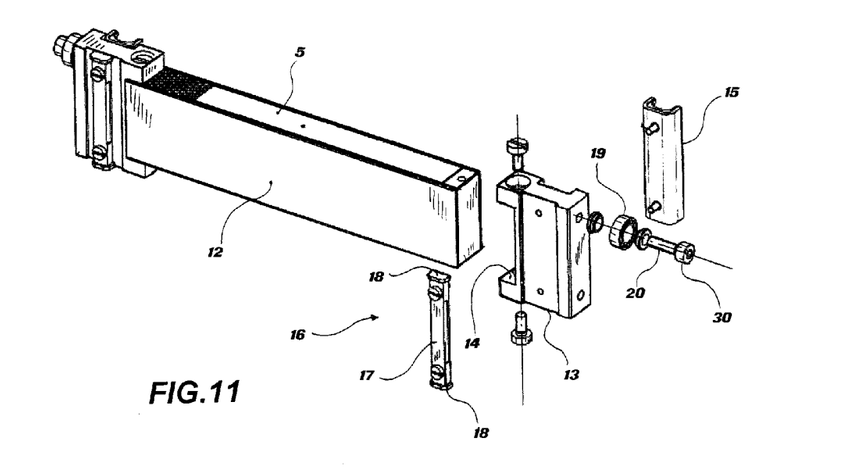
FIG. 11 shows a partially exploded, bottom and overturned axonometric view, of the detail of FIG. 9.

Each fastening member 13 further comprises, at its own outer base, that is on the face directed towards the inner surface of the box-like structure 11, a wheel 19 idly arranged on a pin 20 projecting from the base of the fastening member.

Figure 9:
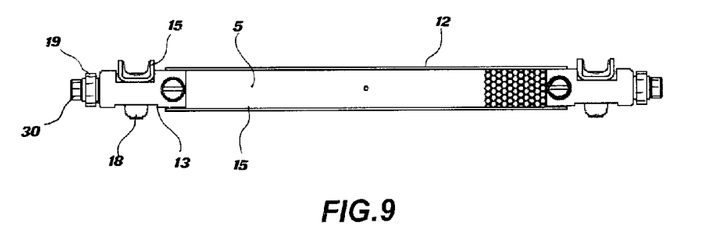
FIG. 9 shows a top plan view of a detail of the collimator of FIG. 5.

The wheel diameter is so that each wheel 19 is in contact with the wheels 19 of the adjacent tubular structures 5; in this way it is possible controlling the tilting of all tubular structures 5 by controlling the tilting of only one thereof, in particular the central one.

To this regard, each pin 20 further comprises a circular head 30 which is destined to be received in a groove 31 formed inside the vertical wall of the box-like structure 11 and on both sides thereof. Each groove 31 is not passing and it has two rectilinear tracts, each tract receiving the heads 30 of the tubular structures 5 on one side and the other one with respect to the central tubular structure.

Furthermore, the head 30 of the central tubular structure is received in a circular recess 32 allowing the rotation only and not the translation of the respective head 30.

Furthermore, the opposite fastening members 13 of the central tubular structure, respectively, comprise in the upper portion thereof a control pin 21 projecting with the face directed towards the inner surface of the box-like structure 11 and passes through the respective vertical wall through a respective slot 22 having a curved, circular profile.

On the outer surface, below the slot 22, the box-like structure 11 has a graduated scale 25 designating the tilting of the inner tubular structures 5.

The control pin 21 is guided along the slot 22 by a jointed crank 23 below the slot 22, on both sides of the box-like structure 11. The joint substantially corresponds to the above-mentioned circular recess 32.

The crank 23 is controlled thanks to a knob 24 arranged on the upper end of the crank itself.

Figure 12A:
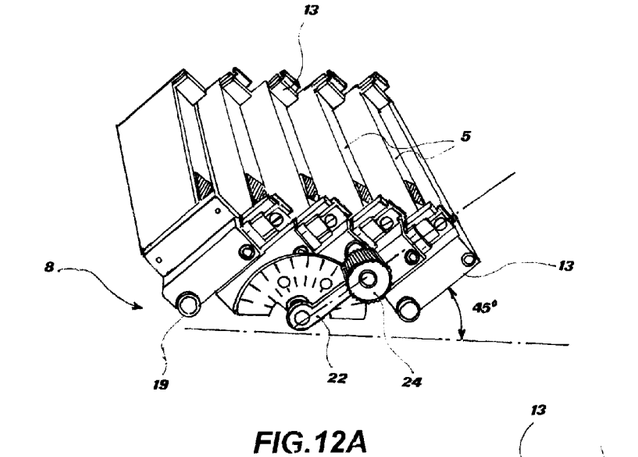
FIGS. 12A, 12B and 12C illustrate the operation of the collimator of FIG. 5.
Figure 12B:
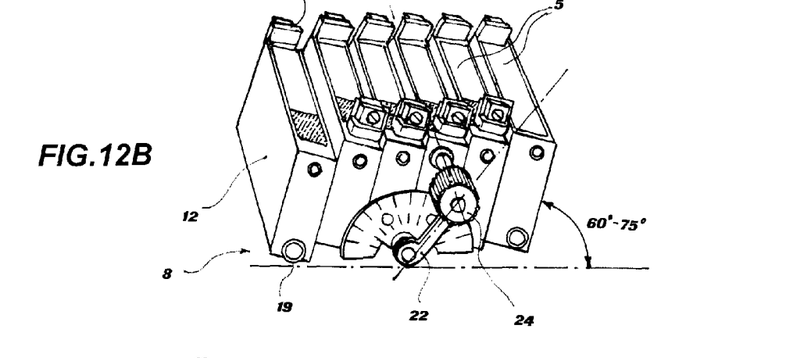
Figure 12C:
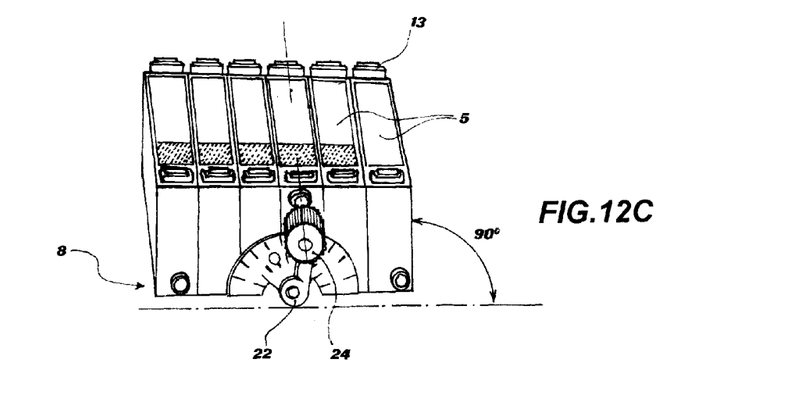

In this way, this simple mechanical system can control again with extreme precision the tilting of the tubular structures inside the box-like structure. A scanning can be then implemented in quick time, by more and more tilting the matrix by an angle with predetermined pitch.

To the above-described tilting collimator a person skilled in the arm, with the purpose of satisfying additional and contingent needs, could introduce several additional modifications and variants, all however within the protective scope of the present invention, as defined by the enclosed claims.

The invention claimed is:
1. A tilting collimator (4), usable in single photon emission computed tomography imaging, comprising:
  a plurality of side-by-side tubular structures (5), configured to form a matrix (7) of tubular structures (5) on a two-dimensional space; each tubular structure (5) being in contact with the tubular structures (5) adjacent thereto so as to be able to tilt only in presence of an equal tilting in the adjacent tubular structures (5), each tubular structure comprising at least one through hole (6); and
  a retaining member (8), acting on the outer edges of said matrix (7), configured to move horizontally to determine the simultaneous tilting of all tubular structures (5) of the matrix (7).

2. The collimator (4) according to claim 1, wherein the tubular structures (5) are metallic and stiff, made of a material impervious to gamma radiation.

3. The collimator (4) according to claim 1, wherein each tubular structure (5) has a substantially parallelepiped-like shape, with plane and smooth outer walls.

4. The collimator (4) according to claim 1, wherein each tubular structure (5) is substantially grid-like shaped implemented by said at least one through hole (6).

5. The collimator (4) according to claim 1, wherein each through hole has a cross size variable from 0.5 to 3.0 mm.

6. The collimator (4) according to claim 1, wherein each tubular structure (5) has a height variable from 10 mm to 50 mm, by guaranteeing that the height is always greater than the cross width of the tubular structure (5).

7. A gamma camera (1) comprising a planar crystal towering above a photomultiplier (2) and constituting the upper face of the gamma camera (1), by providing the resting base for a tilting collimator (4) according to claim 1, configured to select an incidence angle of gamma radiations coming from an organ which is subjected to a single photon emission computed tomography (SPECT).

8. The collimator (4) according to claim 1, wherein the retaining member acts on the two sides parallel to the pushing direction as a guide accompanying the tilting of the tubular structures (5).

9. The collimator (4) according to claim 1, wherein each tubular structure (5) has a bar shape, that is an elongated parallelepiped, its width being so as to allow to implement a certain number of through holes (6), passing through the structure in a height direction.

10. The collimator (4) according to claim 9, wherein the retaining member (8) comprises:
  a pair of slats (12) adhering laterally to the tubular structures (5), so as to contain them; and
  at each end of a tubular structure (5), respective fastening members (13) including a vice (14) which is able to be connected to the end of the tubular structure (5).

11. The collimator (4) according to claim 10, wherein each fastening member (13) comprises, on its own side surfaces, a system of mutual contact constituted on one side by a guide (15), having a recess, and by a corresponding rib (16), shaped so as to be complementary to the recess of the guide (15).

12. The collimator (4) according to claim 9, wherein the tubular structures (5) are received in a box-like structure (11) with a substantially squared shape having a periphery of fixed vertical walls; wherein each fastening member (13) further comprises, at its own outer base, that is on the face directed towards the inner surface of the box-like structure (11), a wheel (19) idly arranged on a pin (20) projecting from the base of the fastening member (15), the wheel diameter being so that each wheel (19) is in contact with the wheels (19) of the adjacent tubular structures (5); and wherein each pin (20) further comprises a head (30) received in a groove (31) formed inside the vertical wall of the box-like structure (11).

13. The collimator (4) according to claim 12, wherein each groove (31) has two rectilinear tracts, each tract receiving the heads (30) on one side and the other one with respect to a central tubular structure, the head (30) of the central tubular structure being received in a circular recess (32) allowing the rotation only and not the translation of the respective head (30).

14. The collimator (4) according to claim 13, wherein the opposed fastening members (13) of the central tubular structure, respectively, comprise, in the upper portion thereof, a control pin (21) projecting with the face directed towards the inner surface of the box-like structure (11) and passes through the respective vertical walls through a respective slot (22) having a bent, circular profile, being provided a jointed crank (23) below the slot (22), on both sides of the box-like structure (11), the joint substantially corresponding to said circular recess (32), the crank (23) being controlled by a knob (24) arranged on the upper end of the crank itself.

15. The collimator (4) according to claim 7, wherein the retaining member acts on tubular structures (5) of the matrix (7) at the respective distal end thereof, that is furthest from the crystal of the gamma camera, or in the immediate proximity.

* * * * *